US008366672B1

(12) United States Patent
Barton et al.

(10) Patent No.: US 8,366,672 B1
(45) Date of Patent: Feb. 5, 2013

(54) FLUID ADMINISTRATION SYSTEM

(76) Inventors: Barry J. Barton, Carrolltown, GA (US);
Rebekah Bacheller, St. Petersburg, FL (US)

( * ) Notice: Subject to any disclaimer, the term of this patent is extended or adjusted under 35 U.S.C. 154(b) by 0 days.

(21) Appl. No.: 13/068,258

(22) Filed: May 6, 2011

(51) Int. Cl.
*A61M 1/00* (2006.01)
(52) U.S. Cl. .................................. 604/151; 600/461
(58) Field of Classification Search ............ 604/65, 604/131, 151; 600/461, 463
See application file for complete search history.

(56) References Cited

U.S. PATENT DOCUMENTS

| 7,244,234 | B2* | 7/2007 | Ridley et al. | 600/459 |
| 7,618,409 | B2* | 11/2009 | Hochman | 604/506 |
| 2004/0215080 | A1* | 10/2004 | Lechner | 600/463 |
| 2011/0202012 | A1* | 8/2011 | Bartlett | 604/218 |

* cited by examiner

*Primary Examiner* — Theodore Stigell

(57) ABSTRACT

A needle has distal, proximal and intermediate extents. The proximal extent has an electrical assembly. A pump has a reservoir. A feed tube operatively couples the reservoir and the needle. An actuator on the electrical assembly is operatively coupled to the pump. The actuator is adapted to activate the pump. In this manner a flow of fluid is fed from the reservoir to and through the needle. A haptic feedback device is operatively coupled to the pump and the electrical assembly. The haptic feedback device is adapted to sense the flow of fluid through the electrical assembly. A sensory signal generator activates the sensory signal generator in response to the sensed flow of fluid through the electrical assembly.

9 Claims, 2 Drawing Sheets

FLUID ADMINISTRATION SYSTEM

BACKGROUND OF THE INVENTION

Field of the Invention

The present invention relates to a fluid administration system and more particularly pertains to assisting a care giver when injecting anesthetic fluid into a patient through a needle, the assisting being through the generating of a sensory signal to the care giver in response to anesthetic fluid flow, the injecting of the anesthetic fluid and the generating of the signal being done in a safe, reliable, convenient and economical manner.

SUMMARY OF THE INVENTION

In view of the disadvantages inherent in the known types of fluid injection systems of known designs and configurations now present in the prior art, the present invention provides an improved fluid administration system. As such, the general purpose of the present invention, which will be described subsequently in greater detail, is to provide a new and improved fluid administration system and method which has all the advantages of the prior art and none of the disadvantages.

To attain this, the present invention essentially comprises a fluid administration system. First provided is a needle. The needle has a distal extent. The needle has a proximal extent. The needle also has an intermediate extent. The intermediate extent is provided between the distal and proximal extents. The distal extent has a patient-injecting point. The proximal extent has an electrical assembly. A passageway is provided through the proximal extent. In this manner anesthetic fluid may flow through. The intermediate extent has a hollow linear feed path. The hollow linear feed path is provided for the anesthetic fluid.

A pump is provided. The pump has a reservoir. The reservoir is adapted to receive and dispense anesthetic fluid. A feed tube is provided. The feed tube operatively couples the reservoir of the pump and the proximal extent of the needle. The electrical assembly has a button. The electrical assembly also has a foot pedal. Primary electrical lines are provided. The primary electrical lines operatively couple the electrical assembly and the pump. The button and/or the foot pedal is adapted to be depressed by the care giver. In this manner, a flow of anesthetic fluid is fed from the reservoir to and through the needle and into the patient.

Provided next is a haptic feedback device. The haptic feedback device has secondary electrical lines. The secondary electrical lines operatively couple the haptic feedback device and the primary electrical lines. The haptic feedback device has tertiary electrical lines. The tertiary electrical lines operatively couple the haptic feedback device and the electrical assembly. The haptic feedback device is adapted to sense the flow of anesthetic fluid through the electrical assembly. The electrical assembly has a sensory signal generator. In this manner the sensory signal generator is activated in response to the sensed flow of fluid through the electrical assembly. The sensory signal generator being chosen from the class of sensory signal generators include a tactile vibrator and an audio buzzer and a visual blinker and an applied force generator. The activating of the sensory signal generator is adapted to provide an indication to the care giver that the anesthetic fluid is flowing without diverting attention of the care giver from the patient.

Further provided is a sonogram detector. The sonogram detector is positionable against the patient in proximity to a location where the needle is inserted into the patient. The sonogram detector has an associated television monitor. The associated television monitor provides viewing by the care provider and others.

Provided last is a source of electrical potential. In this manner the pump, the electrical assembly, the haptic feedback device and sonogram detector are powered.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved fluid administration system which has all of the advantages of the prior art fluid injection systems of known designs and configurations and none of the disadvantages.

It is another object of the present invention to provide a new and improved fluid administration system which may be easily and efficiently manufactured and marketed.

It is further object of the present invention to provide a new and improved fluid administration system which is of durable and reliable constructions.

An even further object of the present invention is to provide a new and improved fluid administration system which is susceptible of a low cost of manufacture with regard to both materials and labor, and which accordingly is then susceptible of low prices of sale to the consuming public, thereby making such fluid administration system economically available to the buying public.

Even still another object of the present invention is to provide a fluid administration system for assisting a care giver when injecting anesthetic fluid into a patient through a needle, the assisting being through the generating of a sensory signal to the care giver in response to anesthetic fluid flow, the injecting of the anesthetic fluid and the generating of the signal being done in a safe, reliable, convenient and economical manner.

Lastly, it is an object of the present invention to provide a new and improved fluid administration system. A needle has distal, proximal and intermediate extents. The proximal extent has an electrical assembly. A pump has a reservoir. A feed tube operatively couples the reservoir and the needle. An actuator on the electrical assembly is operatively coupled to the pump. The actuator is adapted to activate the pump. In this manner a flow of fluid is fed from the reservoir to and through the needle. A haptic feedback device is operatively coupled to the pump and the electrical assembly. The haptic feedback device is adapted to sense the flow of fluid through the electrical assembly. A sensory signal generator activates the sensory signal generator in response to the sensed flow of fluid through the electrical assembly.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated the primary preferred embodiment of the present invention as well as an alternate embodiment of the present invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
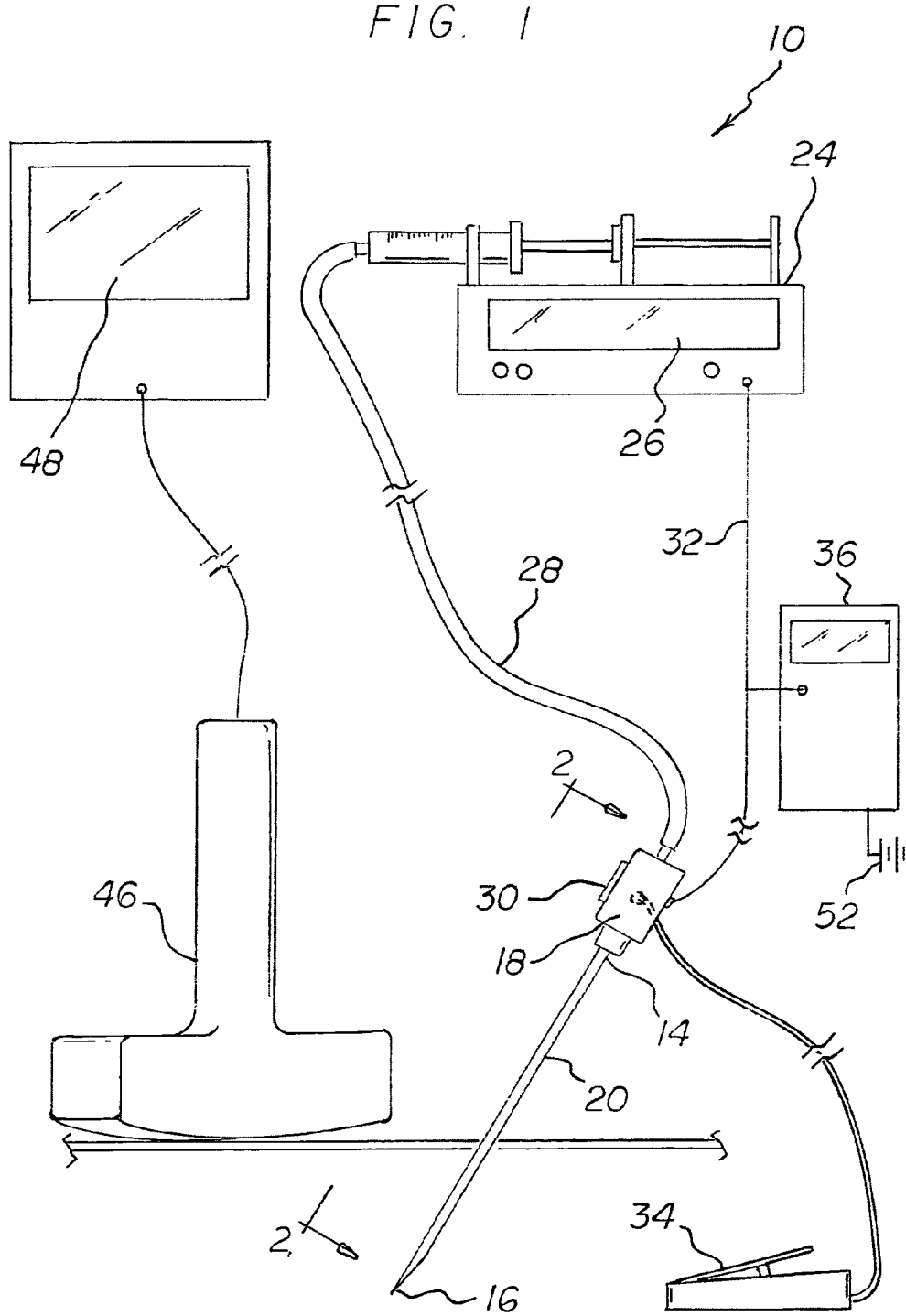
FIG. 1 is a front elevational view of an anesthetic administration system constructed in accordance with the principles of the present invention.
Figure 2:
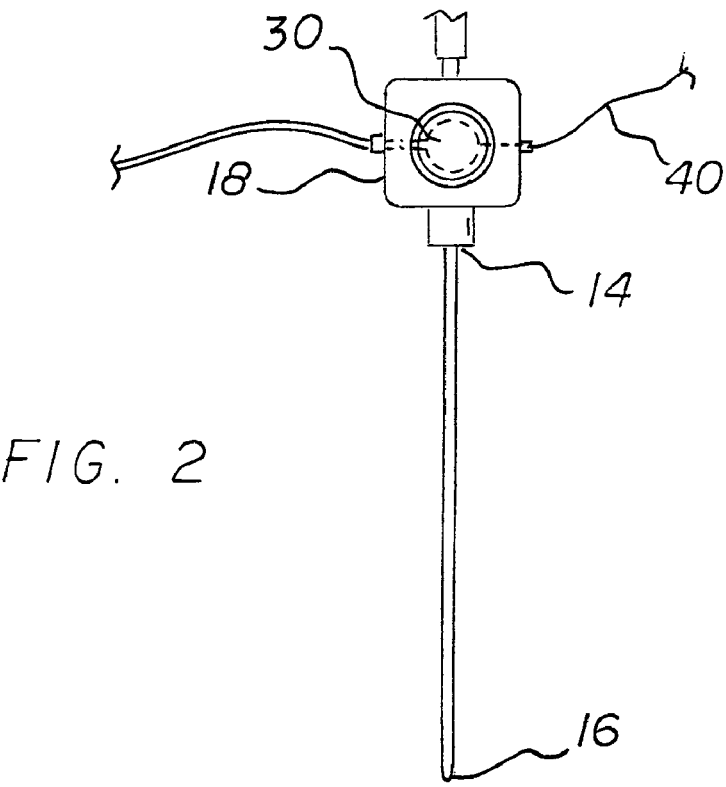
FIG. 2 is a side elevational view taken along line 2-2 of FIG. 1.
Figure 3:
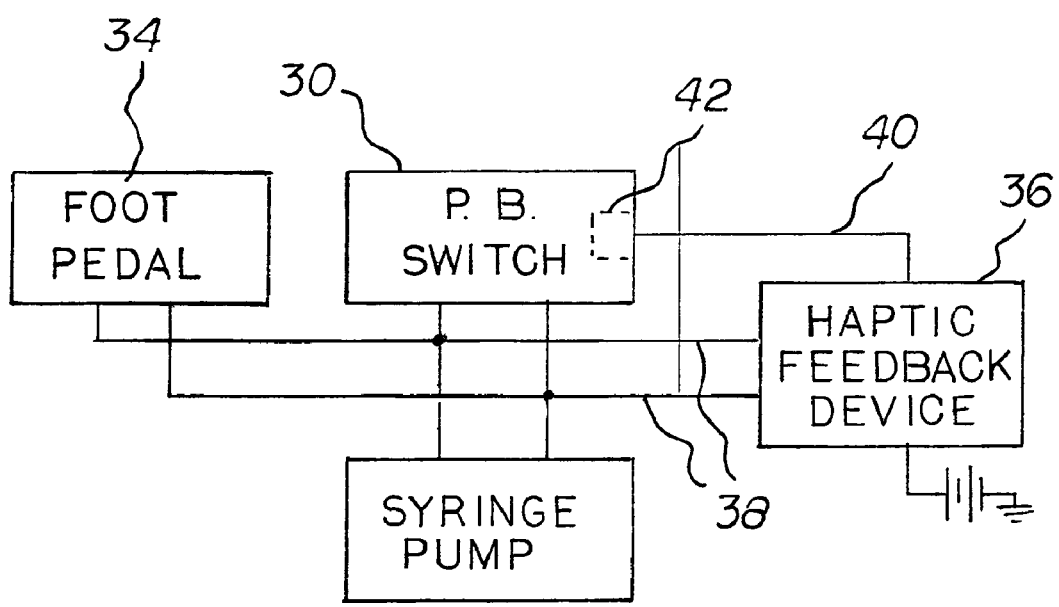
FIG. 3 is an electrical schematic illustration of the system of the prior Figures.

With reference now to the drawings, and in particular to FIG. 1 thereof, the preferred embodiment of the new and improved fluid administration system embodying the principles and concepts of the present invention and generally designated by the reference numeral 10 will be described.

The present invention, the fluid administration system 10 is comprised of a plurality of components. Such components in their broadest context include a needle, a pump and a haptic feedback device. Such components are individually configured and correlated with respect to each other so as to attain the desired objective.

First provided is a needle 14. The needle has a distal extent. The needle has a proximal extent. The needle also has an intermediate extent. The intermediate extent is provided between the distal and proximal extents. The distal extent has a patient-injecting point 16. The proximal extent has an electrical assembly 18. A passageway is provided through the proximal extent. In this manner anesthetic fluid may flow through. The intermediate extent has a hollow linear feed path 20. The hollow linear feed path is provided for the anesthetic fluid.

A pump 24 is provided. The pump has a reservoir 26. The reservoir is adapted to receive and dispense anesthetic fluid. A feed tube 28 is provided. The feed tube operatively couples the reservoir of the pump and the proximal extent of the needle. The electrical assembly has a button 30. The electrical assembly also has a foot pedal 34. Primary electrical lines 32 are provided. The primary electrical lines operatively couple the electrical assembly and the pump. The button and/or the foot pedal is adapted to be depressed by the care giver. In this manner, the pump is activated. Further in this manner a flow of anesthetic fluid is fed from the reservoir to and through the needle and into the patient.

Provided next is a haptic feedback device 36. The haptic feedback device has secondary electrical lines 38. The secondary electrical lines operatively couple the haptic feedback device and the primary electrical lines. The haptic feedback device has tertiary electrical lines 40. The tertiary electrical lines operatively couple the haptic feedback device and the electrical assembly. The haptic feedback device is adapted to sense the flow of anesthetic fluid through the electrical assembly. The electrical assembly has a sensory signal generator 42. In this manner the sensory signal generator is activated in response to the sensed flow of fluid through the electrical assembly. The sensory signal generator being chosen from the class of sensory signal generators include a tactile vibrator and an audio buzzer and a visual blinker and an applied force generator. The term applied force generator is meant that when the care giver pushes on the haptic feedback device, he or she is able to feel an applied force back against the finger to the degree that pressure is building within the delivery system relative to how much the button/pedal is being depressed. The activating of the sensory signal generator is adapted to provide an indication to the care giver that the anesthetic fluid is flowing without diverting attention of the care giver from the patient.

Further provided is a sonogram detector 46. The sonogram detector is positionable against the patient in proximity to a location where the needle is inserted into the patient. The sonogram detector has an associated television monitor 48. The associated television monitor provides viewing by the care provider and others.

Provided last is a source of electrical potential 52. In this manner the pump, the electrical assembly, the haptic feedback device and sonogram detector are powered.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A fluid administration system comprising:
   a needle having distal and proximal and intermediate extents, the proximal extent having an electrical assembly, the electrical assembly including a sensory signal generator;
   a pump having a reservoir, a feed tube operatively coupling the reservoir and the needle, an actuator on the electrical assembly operatively coupled to the pump adapted to activate the pump to feed a flow of fluid from the reservoir to and through the needle; and a haptic feedback device operatively coupled to the pump and the electrical assembly, the haptic feedback device adapted to sense the flow of fluid through the electrical assembly, the sensory signal generator adapted to be activated in response to the sensed flow of fluid through the electrical assembly whereby a care giver using the system will free up his/her hands to both control an injection and to control another location type device.

2. The system as set forth in claim 1 wherein the actuator is a button and a foot pedal.

3. The system as set forth in claim 1 wherein the actuator is a button.

4. The system as set forth in claim 1 wherein the actuator is a foot pedal.

5. The system as set forth in claim 1 wherein the sensory signal generator is chosen from the class of sensory signal generators including a tactile vibrator and an audio buzzer and a visual blinker and an applied force generator, the activating of the sensory signal generator adapted to provide an indication to the care giver that the anesthetic fluid is flowing without diverting attention of the care giver from the patient.

6. The system as set forth in claim 1 and further including:
a sonogram detector positionable against the patient in proximity to a location where the needle is inserted into the patient, the sonogram detector having an associated television monitor for viewing by the care provider and others.

7. The system as set forth in claim 1 and further including:
a source of electrical potential for powering the pump, electrical assembly, haptic feedback device.

8. An anesthetic administration system for assisting a care giver when injecting anesthetic fluid into a patient through a needle, the assisting being through the generating of a sensory signal to the care giver in response to anesthetic fluid flow, the injecting of the anesthetic fluid and the generating of the signal being done in a safe, reliable, convenient and economical manner, the system comprising, in combination:
a needle having a distal extent and a proximal extent and an intermediate extent between the distal and proximal extents, the distal extent having a patient-injecting point, the proximal extent having an electrical assembly and a passageway there through for the flow of anesthetic fluid, the intermediate extent having a hollow linear feed path for the anesthetic fluid;
a pump formed with a reservoir, the reservoir adapted to receive and dispense anesthetic fluid, a feed tube operatively coupling the reservoir of the pump and the proximal extent of the needle, a button in the electrical assembly, a foot pedal in the electrical assembly, primary electrical lines operatively coupling the electrical assembly and the pump, the button and foot pedal adapted to be depressed by the care giver to activate the pump to feed a flow of anesthetic fluid from the reservoir to and through the needle and into the patient;
a haptic feedback device, the haptic feedback device having secondary electrical lines operatively coupling the haptic feedback device and the primary electrical lines, the haptic feedback device having tertiary electrical lines operatively coupling the haptic feedback device and the electrical assembly, the haptic feedback device adapted to sense the flow of anesthetic fluid through the electrical assembly, a sensory signal generator on the electrical assembly adapted to be activated in response to the sensed flow of fluid through the electrical assembly whereby the care giver using the system will free up his/her hands to both control an injection and to control another location type device, the sensory signal generator being a tactile vibrator, the activating of the sensory signal generator adapted to provide an indication to the care giver that the anesthetic fluid is flowing without diverting attention of the care giver from the patient;
a sonogram detector positionable against the patient in proximity to a location where the needle is inserted into the patient, the sonogram detector having an associated television monitor for viewing by the care provider and others; and
a source of electrical potential for powering the pump, electrical assembly, haptic feedback device and the sonogram detector.

9. The system as set forth in claim 1 wherein the sensory signal generator is a tactile vibrator, the activating of the sensory signal generator adapted to provide an indication to the care giver that the anesthetic fluid is flowing without diverting attention of the care giver from the patient.

\* \* \* \* \*